United States Patent [19]

Lowry

[11] Plant 4,315

[45] Oct. 10, 1978

[54] PEAR TREE

[75] Inventor: David B. Lowry, Talent, Oreg.

[73] Assignee: Highcroft Orchards, Talent, Oreg.

[21] Appl. No.: 869,942

[22] Filed: Jan. 16, 1978

[51] Int. Cl.[2] ..... A01H 5/03

[52] U.S. Cl. ..... Plt./36

[58] Field of Search ..... Plt./36

*Primary Examiner*—Robert E. Bagwill

*Attorney, Agent, or Firm*—Roger B. Webster

[57] ABSTRACT

A large, vigorous, upright, tall, vase-formed, rapid growing, hardy pear tree which is foliated with large, obovate, abruptly pointed leaves having a crenate, coarsely serrate margin and a medium length petiole, blooms with pink-white fertile flowers, and a regular and very productive bearer of large to medium size, uniform, obovate, symmetrical fruit—of excellent dessert quality—having a thick, smooth, waxen, glossy skin; the skin having a yellow ground color substantially overspread, in maturity of ripening, with a burgundy red, and the flesh being distinctly white.

1 Drawing Figure

BACKGROUND OF THE VARIETY

1. Field of the Invention

The present variety of pear tree resulted from a plant breeding program conducted by me, and the purpose of which program was the development of new and distinct varieties of pear trees especially adapted to commercial growing. The present variety of pear tree is embraced by Class 36, Plants, of the United States Patent Office MANUAL OF CLASSIFICATION.

2. Prior Varieties

Among the existent varieties of pear trees which are known to me are those mentioned herein for the purpose of comparison; to-wit, Bartlett, Forelle, and Comice (all unpatented).

ORIGIN OF THE VARIETY

The present variety of pear tree was originated by me on a ranch, of which I am an owner, as a cross between the Red Bartlett (unpatented) and the Forelle; such ranch being located in Jackson County, near Talent, Oreg. When the hybrid seedlings resulting from such cross grew to maturity and bore fruit, one such seedling, and which is the present variety, evidenced novel and distinct characteristics. Upon recognition by me of such characteristics, I selected the variety for asexual reproduction preparatory to ultimate commercial growing thereof.

ASEXUAL REPRODUCTION OF THE VARIETY

The present variety of pear tree was asexually reproduced by me as grafts on mature pear trees in an orchard on the aforesaid ranch. In maturity, such asexual reproductions ran true to the original tree in all respects.

SUMMARY OF THE VARIETY

The herein-claimed new and distinct variety of pear tree is large, vigorous, upright, tall, vase-formed, rapid growing, hardy, foliated with large, obovate, abruptly pointed leaves having a crenate, coarsely serrate margin and a medium length petiole, blooms with pink-white, fertile flowers, and a regular and very productive bearer of large to medium size, uniform, obovate, symmetrical fruit —of excellent dessert quality—having a thick, smooth, waxen, glossy skin; the skin having a yellow ground color substantially overspread, in maturity of ripening, with a Burgundy red, and the flesh being distinctly white.

The present variety of pear tree is characterized, in particular comparison to the Bartlett and others, essentially as follows:

TREE STRUCTURE AND GROWTH

Somewhat more upright than Bartlett, being more closely related to the Forelle. New growth tends to grow straight up and is heavier in structure; the new wood tending to be dark.

LEAVES

Slightly larger and slightly wider than Bartlett, but of similar shape; both being tomentose along the midrib on the lower side.

FRUIT BUDS

Medium size with bronze hair on scale surfaces and margins, while Bartlett buds are small with bronze hair on bud scale margins only.

FRUIT

As wide as but shorter than Bartlett, but is pyriform with slightly flattened base. The length/width ratio is 1.23 compared to 1.45 for Bartlett.

The stem averages ¾″ in length and is rather stout, while the stem of the Bartlett averages 4/5″ in length and is slender with an enlargement on the abscission end.

The cavity is deeper than Bartlett, and shallower than Comice.

The basin is distinctly deeper than Bartlett, with closed calyx and inconspicuous lobes below the level of the shoulder. The Bartlett has a very small basin.

The dark or Burgundy red blush of the fruit, in maturity, is uniform around the fruit and not striped in contrast to other varieties.

The dots are slightly submerged as opposed to the Forelle, while the dots of the Bartlett have no areolar condition.

The flesh is distinctly white with a subacid flavor, while the Bartlett has a slightly yellowish-white flesh which is sweet with no indication of acidity.

BRIEF DESCRIPTION OF THE DRAWING:

The drawing is an illustration, by photographic reproduction in color, of a twig with leaves, and detached fruit; with one fruit being in full red color as at maturity of ripening.

DESCRIPTION OF THE VARIETY

The botanical details of this new and distinct variety of pear-tree—with color definitions (except those in common color terms) referenced to Maerz and Paul Dictionary of Color—are as follows:

TREE

Size: Large.
Vigor: Vigorous.
Growth: Upright. Tall. Rapid.
Form: Vase-formed.
Hardiness: Hardy.
Production: Very productive.
Bearing: Regular bearer.

TRUNK

Size: Medium.
Texture: Medium.

BRANCHES

Size: Medium.
Texture: Smooth.
Color:
*Young wood.*—Red.
*Mature wood.*—Brownish gray.
Lenticels:
*Number.*—Medium.
*Size.*—Medium.

LEAVES

Size: Large.
*Length.*—Long — 2½" - 3½".
*Width.*—Wide — 1½" - 2¼".
Form: Ovate. Abruptly pointed.
Thickness: Medium.
Color:
*Top side.*—Red (4-K-11) shading to darker red (7-L-7).
*Under side.*—Samovar yellow (12-K-7).
Texture: Smooth.
Margin: Crenate. Coarsely serrate.
Petiole:
*Length.*—Medium — 1"- 1½".
*Thickness.*—Medium.

BUDS

Size:—Medium.
Texture: Somewhat shaggy on initial opening.

FLOWERS

Blooming period: Medium — April 20th. Slightly later than Bartlett.
Color: Pink on opening, turning to white at full bloom.
Fertility: Fertile.

FRUIT

Ripening period:
*First picking.*—August 30th (ripens after short or thirty-day storage).
*Last picking.*—October 15th.
*Length of season.* —3 weeks.
Retention: Hangs well.
Size: Large to medium — 2¾" average. Uniform.

Form: Obovate. Symmetrical. Uniform.
Stem: Medium length — Average ¾" Medium thickness.
Cavity: Acute. Medium depth. Narrow. Smooth. Symmetrical.
Calyx: Closed. Small.
*Lobes.*—No separation at base. Short. Broad. Obtuse.
Basin: Medium depth. Medium width. Symmetrical. Rounded. Obtuse. Smooth.

SKIN

Thickness: Thick.
Texture: Smooth. Waxen. Glossy.
Color: Yellow (11-L-5) ground color overspread, in maturity, with Burgundy red (7-J-6), with numerous medium-size submerged red dots.

FLESH

Color: White (9-B-1).
Texture: Firm — fine. Tender. Juicy.
Flavor: Subacid. Aromatic.
Eating quality: Excellent.
Core: Medium size. Closed. Axile.
Core lines: Meeting.
Calyx tube:
*Length.*—Medium.
*Width.*—Medium.
*Form.*—Funnel-shaped.
Seed: Medium size. Plump. Acute.

USE

Desert. Market.

KEEPING QUALITY

Good — up to 20 weeks.

SHIPPING QUALITY

Good.

RESISTANCE TO INSECTS AND DISEASES

Midway between Bartlett and Forelle; being more resistant to pear blight than Forelle. Does not demonstrate any form of virus, and no unusual problems with insects or diseases.

VARIANCE IN BOTANICAL DETAILS

The pear tree and its fruit herein described may vary in slight detail due to climatic and soil conditions under which the variety may be grown; the present description being of the variety as grown in the Jackson County area of Oreg.

I claim:

1. A new and distinct variety of pear tree, substantially as illustrated and described, which is large, vigorous, upright, tall, vase-formed, rapid growing, hardy, foliated with large, obovate, abruptly pointed leaves having a crenate, coarsely serrate margin and a medium length petiole, blooms with pink-white, fertile flowers, and a regular and very productive bearer of large to medium size, uniform, obovate, symmetrical fruit —of excellent dessert quality—having a thick, smooth, waxen, glossy skin; the skin having a yellow ground color substantially overspread, in maturity of ripening, with a Burgundy red, and the flesh being distinctly white; and the fruit, in comparison to the Bartlett, being shorter and pyriform with a slightly flattened base, the red of the skin being more uniform about the fruit, and the distinctly white flesh being subacid whereas the flesh of the Bartlett is yellowish-white and sweet.

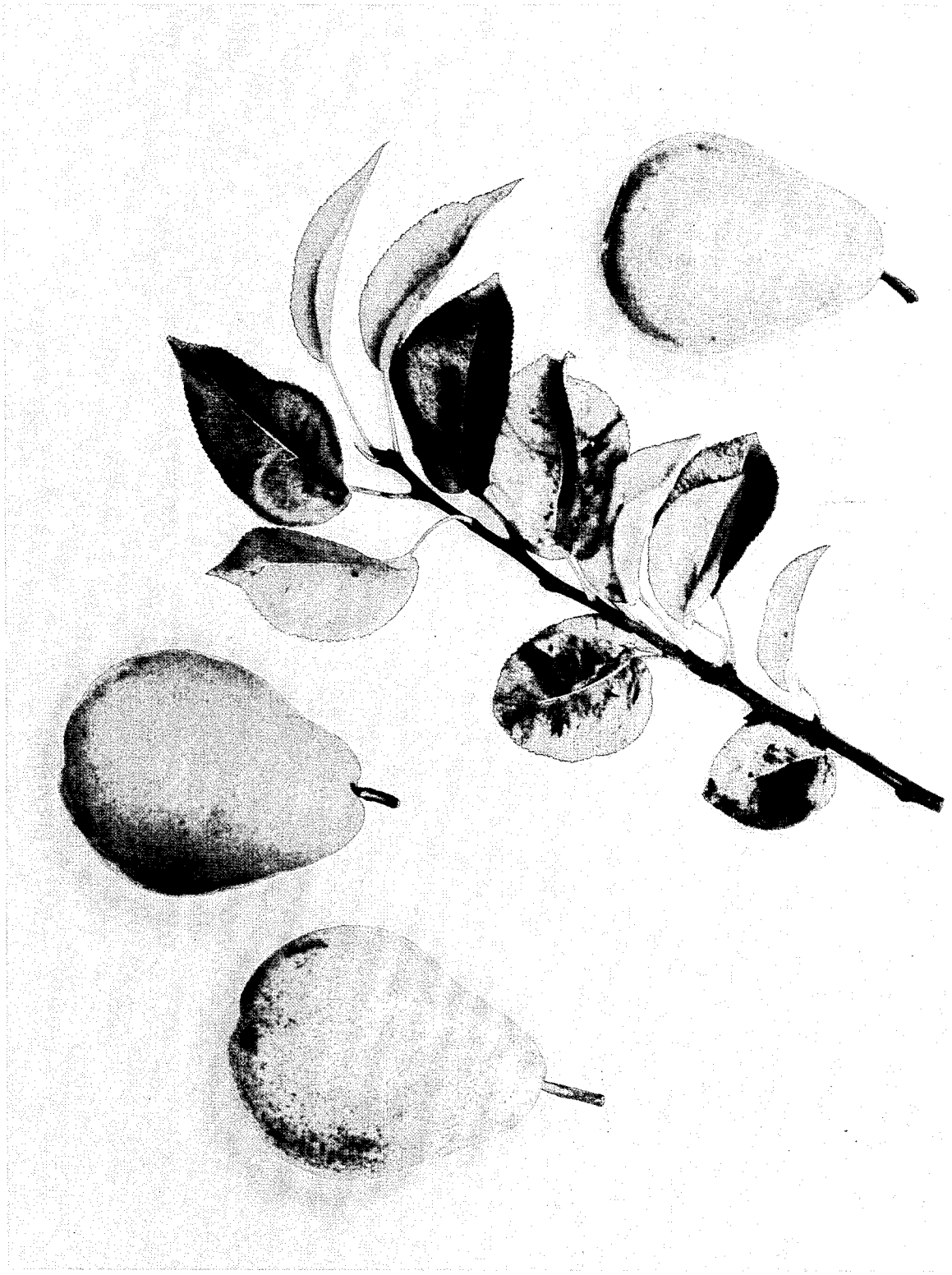

* * * * *